US010151735B2

(12) United States Patent
Joplin

(10) Patent No.: US 10,151,735 B2
(45) Date of Patent: *Dec. 11, 2018

(54) SOLID CONTENTS VERIFICATION SYSTEMS AND METHODS

(71) Applicant: EXPRESS SCRIPTS, INC., St. Louis, MO (US)

(72) Inventor: Jonathan W. Joplin, Chesterfield, MO (US)

(73) Assignee: EXPRESS SCRIPTS STRATEGIC DEVELOPMENT, INC., St. Louis, MO (US)

( * ) Notice: Subject to any disclaimer, the term of this patent is extended or adjusted under 35 U.S.C. 154(b) by 153 days.

This patent is subject to a terminal disclaimer.

(21) Appl. No.: 15/342,547

(22) Filed: Nov. 3, 2016

(65) Prior Publication Data

US 2017/0074851 A1 Mar. 16, 2017

Related U.S. Application Data

(63) Continuation of application No. 14/274,880, filed on May 12, 2014, now Pat. No. 9,513,259, which is a
(Continued)

(51) Int. Cl.
G01N 29/07 (2006.01)
G01N 29/04 (2006.01)
G01N 29/11 (2006.01)
G06F 17/00 (2006.01)
G06F 7/00 (2006.01)
(Continued)

(52) U.S. Cl.
CPC ............. *G01N 33/15* (2013.01); *G01B 11/24* (2013.01); *G01F 23/2962* (2013.01); *G01J 3/50* (2013.01); *G01N 29/043* (2013.01); *G01N 29/07* (2013.01); *G01N 29/11* (2013.01); *G01N 29/12* (2013.01); *G01V 1/00* (2013.01); *G01N 2291/011* (2013.01); *G01N 2291/02408* (2013.01); *G01N 2291/044* (2013.01)

(58) Field of Classification Search
CPC ....... G01N 29/043; G01N 29/07; G01N 29/11
See application file for complete search history.

(56) References Cited

U.S. PATENT DOCUMENTS 3,881,353 A 5/1975 Fathauer
4,114,441 A 9/1978 Magri
(Continued)

*Primary Examiner* — Helen Kwok
(74) *Attorney, Agent, or Firm* — Bryan Cave Leighton PaisnerLLP

(57) ABSTRACT

Solid contents verification systems and methods are provided. The system includes a contents sensor unit, a container-carrying unit and a control unit. The contents sensor unit has at least one contents sensor configured to send and receive sonic pulses to determine a state of contents in a container. The contents sensor unit is configured to send a signal communicating a state of the contents in a container. The container-carrying unit is configured to hold a container in substantial alignment with the contents sensors to expose the contents to the sonic pulses. The control unit is operatively connected to the contents sensor unit. The control unit is configured to receive the signal communicating the state of the contents and to compare the state of the contents with a desired state of the contents.

22 Claims, 4 Drawing Sheets

Related U.S. Application Data continuation of application No. 13/300,303, filed on Nov. 18, 2011, now Pat. No. 8,756,998.

(60) Provisional application No. 61/449,573, filed on Mar. 4, 2011.

(51) Int. Cl.
*G01N 33/15* (2006.01)
*G01B 11/24* (2006.01)
*G01F 23/296* (2006.01)
*G01J 3/50* (2006.01)
*G01N 29/12* (2006.01)
*G01V 1/00* (2006.01)

(56) References Cited

U.S. PATENT DOCUMENTS

| | | |
|---|---|---|
| 4,182,451 A | 1/1980 | Watson |
| 4,208,915 A | 1/1980 | Edwards |
| 4,187,718 A | 2/1980 | Shibasaki |
| 4,223,790 A | 9/1980 | Yoshida |
| 4,332,016 A | 5/1982 | Bernstein |
| 4,821,573 A | 4/1989 | Nagata et al. |
| 5,684,252 A | 11/1997 | Kessler et al. |
| 5,768,939 A | 6/1998 | Quayle |
| 5,869,747 A | 2/1999 | Hulsman |
| 5,929,337 A | 7/1999 | Collins et al. |
| 6,035,718 A | 3/2000 | Lucas |
| 6,092,419 A | 7/2000 | Dixon et al. |
| 6,182,511 B1 | 2/2001 | Lucas |
| 6,234,023 B1 | 5/2001 | Collins et al. |
| 6,357,136 B1 | 3/2002 | Erickson et al. |
| 6,484,121 B1 | 11/2002 | Filev et al. |
| 6,769,307 B1 | 8/2004 | Dixon et al. |
| 7,107,852 B2 | 9/2006 | Hutchins et al. |
| 8,096,183 B2 | 1/2012 | Knittel et al. |
| 8,459,120 B2 | 6/2013 | Keeton et al. |
| 8,756,998 B1 * | 6/2014 | Joplin ............... G01N 29/11 221/2 |
| 9,513,259 B2 * | 12/2016 | Joplin ............... G01N 29/11 |
| 2004/0035208 A1 | 2/2004 | Diaz |
| 2006/0123911 A1 | 6/2006 | Basir et al. |
| 2007/0084287 A1 | 4/2007 | Binkley et al. |
| 2012/0090961 A1 | 4/2012 | De Martin |

\* cited by examiner

SOLID CONTENTS VERIFICATION SYSTEMS AND METHODS

CROSS-REFERENCE TO A RELATED APPLICATION

This application claims priority under 35 U.S.C. § 119(e) to U.S. Provisional Patent Application No. 61/449,573 filed on Mar. 4, 2011. The entire disclosure of U.S. Provisional Patent Application No. 61/449,573 is hereby incorporated herein by reference.

FIELD

This application generally relates to solid contents verification system and method. More specifically, this application relates to solid contents verification system and method for determining a state of contents in a container.

BACKGROUND

High volume pharmacies process and fill a large number of prescriptions per day. These pharmacies often rely on automated systems to process and fill the prescriptions. Many of the high volume pharmacies have various verification procedures to ensure that a container, labeled for a specific drug in a specific quantity for a specific patient, is correctly dispensed. In a retail pharmacy environment, the Pharmacist will typically either hand count pills or use a pill counting mechanism to verify the count. This is a very manual process, and pill counting mechanisms are subject to error. In high volume pharmacies, where extremely high volumes of prescriptions are dispensed, the counting is performed automatically. It would be difficult if not impossible to verify all of the automatically dispensed prescriptions for count accuracy using pharmacists to count every pill by hand or even using a pill counting mechanism, such as Torbal weigh scales, Kirby Lester, or GSE Eyecon visual prescription counting systems.

DETAILED DESCRIPTION

Example methods and systems for solid contents verification are described. In the following description, for purposes of explanation, numerous specific details are set forth in order to provide a thorough understanding of example embodiments. It will be evident, however, to one of ordinary skill in the art that embodiments of the invention may be practiced without these specific details.

Generally, contents in a container are verified by utilizing one or more contents sensors. The contents sensors are directed at an opening of the container and generate a signal based on the amount, presence or absence of contents in the container.

The signal is used to determine a state of the contents in the container. The state of the contents is compared with a desired state of the contents. Based on this comparison, the container is either considered verified and correct or is flagged for inspection.

Figure 1:
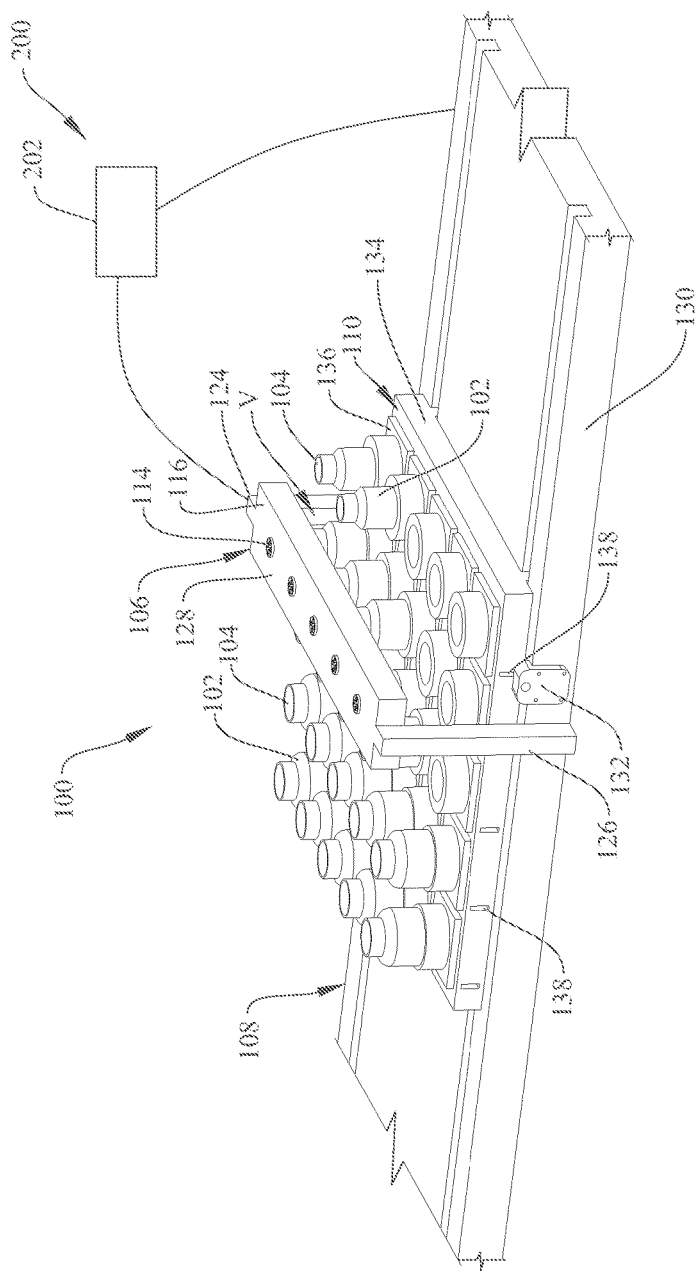
FIG. 1 is perspective view of a solid contents verification system.

Referring initially to FIG. 1, a solid contents verification system 100 is illustrated in accordance with an embodiment. As used herein, container 102 means a hollow structure or receptacle that is generally closed by walls except for an opening 104 to receive the contents. The walls of the container 102 may have characteristics to protect the contents stored therein from the environment. In some embodiments, the container 102 is waterproof or at least moisture resistant. The walls of the container 102 may further be air or gas impermeable or at least resistant to gas flow to prevent or reduce outgassing from the interior of the container 102 to the environment. The state of the contents may include a level of an upper surface of the contents relative a top or bottom of the container 102, the quantity of the contents in the container 102, the presence of the contents in the container 102, an absence of the contents from the container 102, or combinations thereof, for example. The solid contents verification system 100 compares the state of the contents in the container with a state to verify that the state of the contents in the container 102 is proper. In some embodiments, the state of the container 102 for a certain type of container, select type of content, and the quantity of content can be predetermined and stored in a memory (e.g., a memory on board the system 100 or in a database that is in electrical communication with the solid contents verification system 100). In the case of storing the state in a remote memory, the system 100 may download the state based on a filling instructions, e.g., a prescription, that are to be filled for a certain period of time, e.g., day, hour, or other, or based on a run of the solid contents verification system 100.

As used herein, contents can mean multiple small, pellet-like materials that may be contained in the container 102. In some embodiments, there can be numerous contents that can be stored in a single container. The contents may be tablets, powders, liquids, transdermal patches, capsules, troches, and the like. The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and/or a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active component, sucrose or fructose as a sweetening agent, methyl and propyl parabens as preservatives, a dye and flavoring such as cherry or orange flavor. Any material used in preparing a unit dosage form of the content should be pharmaceutically acceptable and substantially non-toxic in the amounts employed. In addition, the active component may be incorporated into sustained-release preparations and devices. The above types of contents and the variations of the components of the contents may interact with the methods and structures to verify the contents stored in a container. In some embodiments, the structure of an individual type of content may provide a different sensed signal as compared to another type of content.

The solid contents verification system 100 includes a contents sensor unit 106, a conveyor unit 108, at least one container-carrying unit 110 and a verification subsystem 200 having a control unit 202. The contents sensor unit 106 is disposed at the conveyor unit 108 to acquire information about the contents held by the container-carrying unit 110. The container-carrying unit 110 is movably disposed at the conveyor unit 108, which moves the container-carrying unit 110 to and from the contents sensor unit 106. In some embodiments, the contents sensor unit 106 can move relative to the container-carrying unit 110. The control unit 202 is communicatively connected to the contents sensor unit 106 and the conveyor unit 108, both of which send and receive information, such as data and instructions, to and from the control unit 202.

The contents sensor unit 106 includes contents sensors 114 and a sensor support structure 116. A single content sensor 114 or multiple content sensors 114 may be included. The sensor support structure 116 supports the contents sensors 114 and positions the contents sensor 114 for viewing the container-carrying unit 110 and, hence, the container(s) 102, as it moves along the conveyor unit 108. The solid contents verification system 100 provides contents sensors 114 that do not require placement against the container 102. That is, the contents sensor unit 106 functions at a distance removed from the container 102 and need not make physical or mechanical contact with the container 102.

The contents sensor 114 may include a sound pulse device that both sends and receives sonic pulses. An example of the contents sensor 114 that has a sound pulse device includes a U GAGE Q45U ultrasonic sensor from Banner Engineering, Corp., Minneapolis, Minn. The contents sensor 114 may have separate transducers for sending and receiving. In this embodiment, however, the contents sensor 114 includes a transceiver member 118. The transceiver member 118 has a transceiver that both sends and receives sonic pulses. Reflected sonic pulses are received by the transceiver member 118 and translated into a signal. In some embodiments, the transceiver member 118 can include a transducer that converts the sound pulse into an electrical signal. The transceiver member 118 may include circuitry to determine a distance to a target object, such as a reflective upper surface of the contents in the container 102 a bottom of the container in the case of an empty container or when the sound pulse reflects off the bottom surface, or both. The contents sensor 114 is at least substantially aligned with the opening 104 so as to direct the sonic pulses through the opening 104 for reflection by the contents. Measuring time from transmission of a burst of sonic pulses until receipt of reflected sonic pulses or echoes facilitates the determination of distance to the target object. The contents sensor 114 can use ultrasonic pulses, pulsed radar or microwave signals, or other electromagnetic signals. In the case of electro-magnetic signals, the contents sensor 114 may include photo diodes, CMOs detectors, and the like to detect the reflected signals from the interior of the container 104. In other embodiments, light can be used as the measurement device, such as LIDAR or time of flight camera technology. The contents sensor 114 sends a signal to the control unit 202 representing the distance or merely representing the amount of measured time from transmission to receipt of the sonic pulses. The contents sensor 114 may be configured with processing capabilities (e.g., with dedicated circuitry, processor, or programmable logic arrays, etc.) to determine the distance and to send the signal that includes data or may communicate the distance or time. For example, in the instant embodiment, the signal is a voltage signal sent to the control unit 202. Such a voltage signal can represent digital information in with the voltage levels representing ones or zeros in digital communication.

Referring again to FIG. 1, the sensor support structure 116 supports the contents sensors 114 above the conveyor unit 108 to provide a clear view into the container(s) 102 for the transceiver member 118. Specifically, the sensor support structure 116 includes a first support member 124, a second support member 126 and a support platform 128. The first and second support members 124, 126 extend substantially perpendicularly from respective ends of the support platform 128. The support platform 128 holds the contents sensors 114 at the position above the conveyor unit 108. In this embodiment, an end portion of the first and second support members 124, 126 are fixedly attached to the conveyor unit 108. In other embodiments, the first and second support members 124, 126 may extend upwardly from the support platform 128 and be fixed above the conveyor unit 108 to hang the support platform 128 above the conveyor unit 108. Establishing the position above the conveyor unit 108 provides a clear view for the contents sensors 114 to send and receive sonic pulses (or other electro-magnetic signals) to and from the container-carrying unit 110. The distance from the support platform 128 and/or the contents sensors 114 to the container-carrying unit 110 may be determined before the containers are measured. This distance can be fixed at the time of installation of the solid contents verification system 100.

The conveyor unit 108 includes a conveyor support structure 130, an actuator assembly (not shown) and a position sensor 132. The conveyor support structure 130 supports the position sensor 132 in an operable position. The support structure 130 may have multiple support legs and a platform, for example. The actuator assembly includes a belt, cable or chain, for example, which engages the container-carrying unit 110 so as to move the container-carrying unit 110 along a length of the conveyor unit 108. The actuator assembly further includes an actuator (not shown), such as a motor to movably engage the belt, cable or chain. In another embodiment, the actuator assembly includes a conventional linear motor that moves the container-carrying unit 110 via magnets fixed to the container-carrying unit 110.

The container-carrying unit 110 includes a base 134, one or more container chamber sections 136 and one or more position indicators 138. The base 134 may be a carton, pallet, tote or tray, for example, which contacts the conveyor unit 108. The base 134 encompasses the one or more container chamber sections 136 that are arranged in an orderly fashion, such as the matrix, e.g., the rows and the columns shown in FIG. 1. The container chamber sections 136 has a chamber sized and configured to receive the container 102 therein. The container chamber sections 136 secure the container 102 within the container structure 134 to facilitate substantial alignment of the container 102 with one of the contents sensors 114. Various sized container chamber sections 136 are typically provided in the container structure 134 to transport the containers 102 of different sizes, e.g., different diameters, different heights, different exterior configurations (cylindrical, conical, polygonal, or combinations thereof) along a length of the conveyor unit 108.

The container-carrying unit 110 may be made of polymer materials so as to provide a contrast with the position indicator 138, which is made of a different material, e.g., metallic. The position indicator 138 is disposed on the container-carrying unit 110 to indicate a relative position of the container-carrying unit 110 on the conveyor unit 108 to the position sensor 132. In this embodiment, the container chamber sections 136 are arranged in rows and columns on the container structure 134. The position indicator 138 is positioned on the container structure 134 at an end of the row to indicate the position of the row on the conveyor unit 108. Multiple position indicators 138 may be used for multiple rows. In this embodiment, the position sensor 132 is an inductive sensor, such as that from Turck, Inc., Plymouth, Minn., that senses proximity of the position indicator 138. The position sensor 132 is configured to send a signal to the control unit 202 indicating the presence of the position indicator 138. The control unit 202 is configured to utilize such signals in the controlling of the actuator assembly of the conveyor unit 108, as will be explained below.

In some embodiments, the position sensor 132 is fixed to the contents sensor support structure 116 and the position indicator 138 is fixed to an upper surface of the container structure 134. In some embodiments, the position sensor 132 and the position indicator 138 may be fixed from various positions and angles so long as the position sensor 132 is able to recognize the proximity of the position indicator 138.

Figure 2:
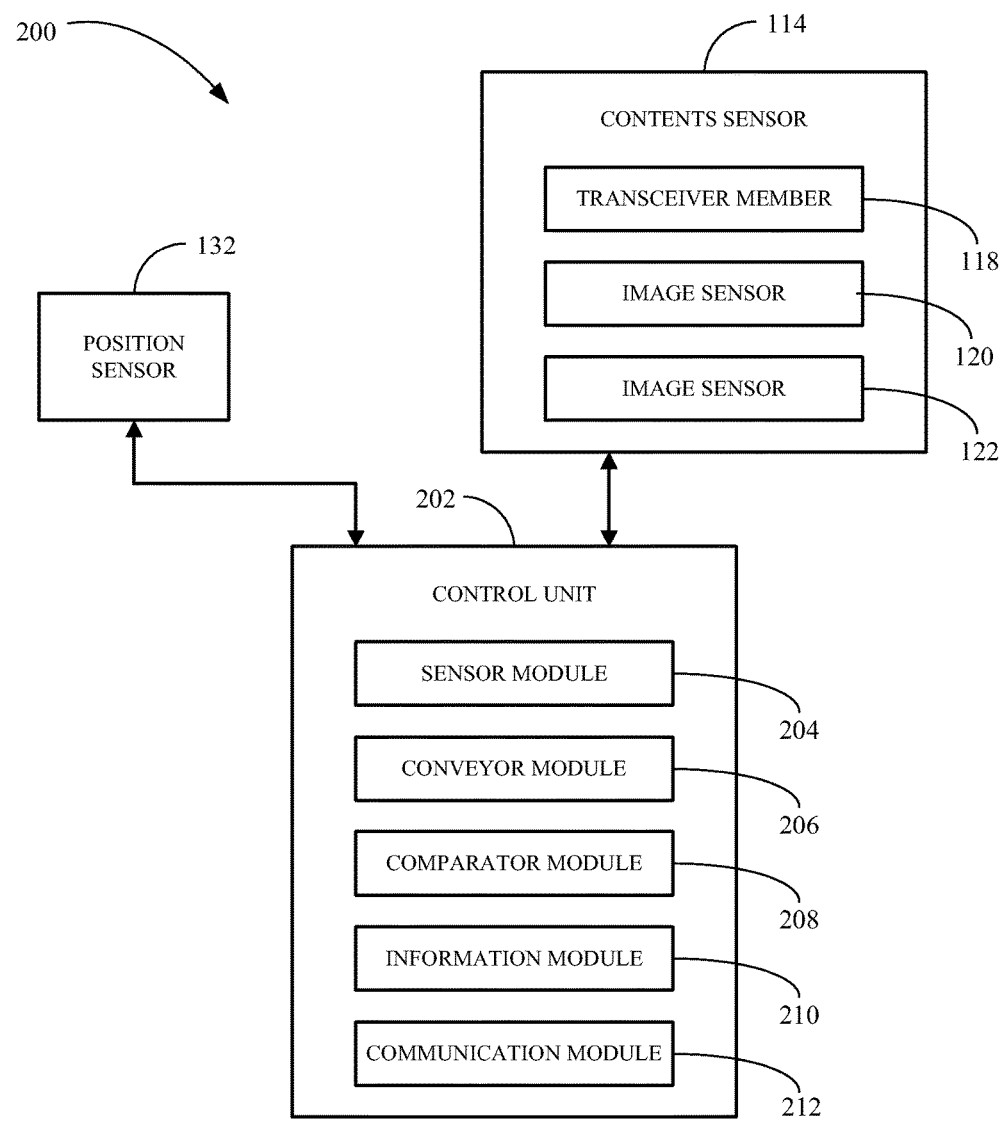
FIG. 2 is a block diagram of sensors and a control unit of the solid contents verification system.

FIG. 2 shows the verification subsystem 200 having the contents sensor 114 that, in one embodiment, includes first and second image sensors 120, 122 connected to the control unit 202. The first image sensor 120, located proximal to the transceiver member 118, captures images of the contents that are analyzed with shape or color recognition algorithms to determine other states of the contents, such as an unwanted mix of different types of contents. In other embodiments, the first image sensor 120 may be disposed separately from the contents sensor 114 and capture images independently of the contents sensor 114. An example of the first image sensor 120 that may be used is a PresencePLUS P4 Omni vision sensor with accompanying software from Banner Engineering, Corp., Minneapolis, Minn. The second image sensor 122 may be separate from the transceiver member 118 and positioned to acquire an image of a label on the container 102. An example of the second image sensor 122 that may be used is a Teledyne DALSA camera from Teledyne DALSA, Waterloo, Ontario, Calif. The acquired image is read to acquire container-specific information regarding the intended contents of the container 102. Software for acquiring the container-specific information from the image may be from Automated Vision LLC, Madison, Wis., for example. The container-specific information, such as quantity of contents, container size and/or type of contents, is used by the control unit 202 to obtain the predetermined state for that particular container 102. The contents sensor 114 may include circuitry or a processor to perform the functions of the contents sensor 114 described herein.

Referring to FIG. 2, the control unit 202 includes a sensor module 204, a conveyor module 206, a comparator module 208, an information module 210 and a communication module 212.

The control unit 202 further includes a microcomputer running a control program on a processor circuit to control the functions of the components as discussed herein. The control unit 202 may also include other conventional components, such as input and output interface circuits, and memory devices, such as a ROM device, a RAM device and/or a NVRAM device. The memory devices may store processing results and control programs for one or more of the components' functions. The control unit 202 is operatively connected to the contents sensor unit 106 and the conveyor unit 108 in a conventional manner Further, the control unit 202 is capable of selectively controlling any of the components in accordance with the control programs. The term "configured" as used herein to describe a component of the control unit 202 includes hardware and/or software that is constructed and/or programmed to carry out the desired function. Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The control unit 202 controls various functions of the contents sensor unit 106 and the conveyor unit 108. Specifically, the sensor module 204 is configured to manage communications signals to and from the contents sensors 114. The sensor module 204 may have a processor for signal processing. The conveyor module 206 manages control instructions to operate the conveyor unit 108. The comparator module 208 receives information regarding the state of the contents from the contents sensors 114 and compares the state with the stored state. The comparator module 208 may have a processor for signal processing in addition to or instead of the signal processing by the sensor module 204. The information module 210 stores states for various types of contents and containers. The states can be predetermined for various types of containers and contents. The communication module 212 manages communication with the transceiver member 118, the image sensors 120, 122 and the position sensor 132.

Figure 3:
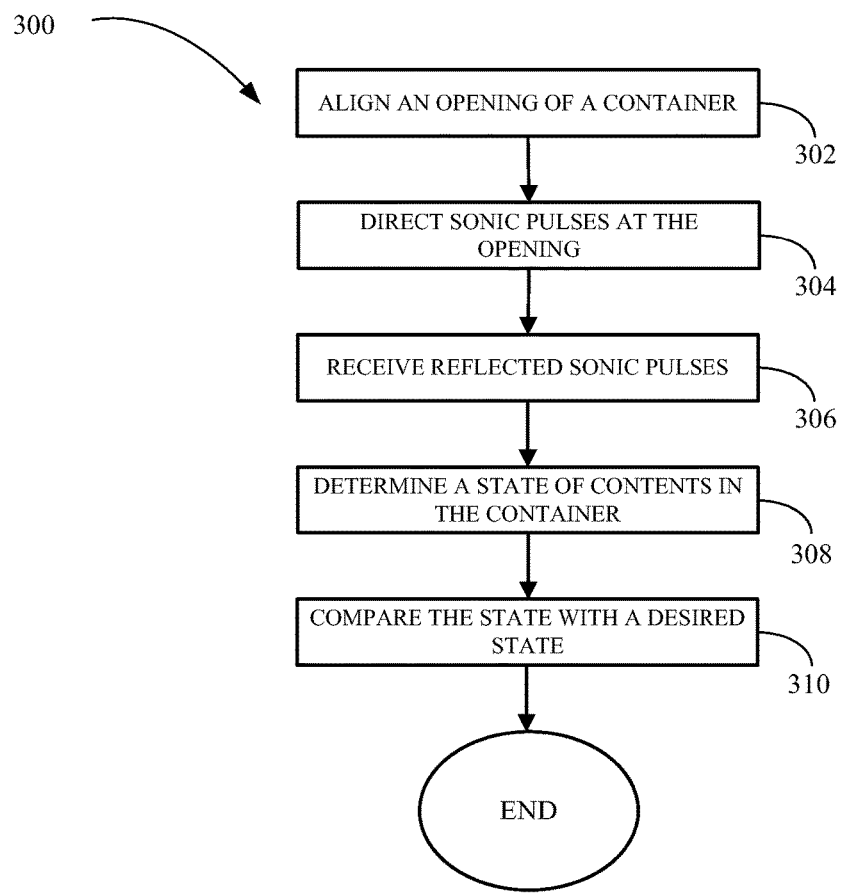
FIG. 3 is a chart of a solid contents verification method.

Referring to FIG. 3, a solid contents verification method 300 includes aligning an opening 104 of the container 102 with the contents sensor 114 at a verification point V (FIG. 1) at block 302 of the method 300. In the case of multiple contents sensors 114, the contents sensors 114 are spaced apart at the support structure 116 to substantially align, from above, with the container chamber sections 136 and therefore openings 104 of the containers 102. The verification point V is an area under the contents sensors 114. Specifically, the area under the contents sensors 114 that allows the at least substantial alignment with the opening 104 of the container 102 is considered the verification point V. For example, in the solid contents verification system 100 of FIG. 1, the contents sensors 114 in a row are substantially aligned at an appropriate angle with a row of container chamber sections 136 having containers 102 at the verification point V. The position sensor 132 is located at a location on the conveyor unit 108 to detect the position indicator 138 at the verification point V. At the verification point V, the position sensor 132 detects the position indicator 138 and sends a row detection signal. The row detection signal is transmitted from the position sensor 132 to the control unit 202 and, in an example embodiment, the container-carrying unit 110 is stopped by the control unit 202. The conveyor unit 108 may have one or more stops, such as the VE 2/D-60 cushioned stop gate from Bosch Rexroth AG, Stuttgart, Germany, that is engaged by the control unit 202 to stop the container-carrying unit 110 at the verification point V.

At the verification point V, the control unit 202 instructs the contents sensor 114 to direct sonic pulses at the opening 104 as in block 304. With the opening of the container 104 opening upwardly, and the content sensor(s) 114 sending measurement signals downwardly into the container 104, the measurement signals need not pass through the wall of the container 104. In some embodiments, the measurement signals contact the contents of container prior to contacting the container walls, unless the container is empty. At block 306, the transceiver member 118 of the contents sensor 114 receives sonic pulses that are reflected by contents in the container 102 and/or reflected by the bottom of the container 102, in the case of an empty or nearly empty container 102. The contents sensor 114, using the received reflected sonic pulses and time to receive the reflected sonic pulses, determines a state of the contents in the container 102 with a processor, for example, (block 308) and transmits the state of the contents to the control unit 202. In one embodiment, the control unit 202 receives data on the received reflected sonic pulses and the time for receiving the reflected sonic pulses from the contents sensor 114. The control unit 202 then processes the data to determine the state of the contents in the container 102.

The control unit 202 compares the state of the contents in the container with a desired or predicted state of the contents, as in block 310. The predicted state may be acquired at the information module 210. The information module 210 may have multiple stored states categorized by characteristics of the contents, for example. That is, a stored state of contents in a particular container 102 may be accessed in the information module 210 by referencing size, color, name, quantity, etc. of the contents. The type of content and its coating may also affect the desired state. The comparator module 208 may compare the state of the contents in the container 102 with the stored state of the contents. Should the state of the contents be substantially inconsistent with the stored state, the comparator module 208 may send an alert signal via the communication module 212 to an operator. The method 300 is repeatable for multiple container structures 134 having multiple containers 102 of various sizes and having various types and quantities of contents. In an example embodiment, each of the multiple container structures can have an individual return signal that can be used in the comparator module 208 to correct for the type of container. The method 300 may also be performed simultaneously with multiple contents sensors 114.

The control unit 202 may obtain characteristics of the contents for use in acquiring the stored state by manual entry from an operator, for example. The control unit 202 may also utilize the first image sensor 120 and/or the second image sensor 122 to obtain characteristics of the contents in the container 102. The first image sensor 120 is configured and arranged to acquire an image of the contents in the container 102. The control unit 202 may then analyze the image to determine characteristics, e.g., shape and/or color, of the contents of the container. The control unit 202 may then utilize the obtained characteristics to access the corresponding stored state for the container 102. The control unit 202 may also utilize the analyzed image to compare the shape and color with the stored, desired state.

The second image sensor 122 is configured and arranged to acquire an image of a label of the container 102 having container-specific information. The control unit 202 may then analyze the image of the label to determine characteristics, e.g., name, quantity, etc., of the contents to access the stored state for that container 102.

If the comparison by the comparator module 208 results in comparison in which the state of the contents is substantially inconsistent with the desired state, the control unit 202 may identify or flag the container 102. The conveyor module 206 may then instruct the conveyor unit 108 to route the container 102 to an inspection station. Thus, the contents verification system 100 and method 300 may assess containers 102 and intervene by physically separating selected containers 102 from other containers 102 if the state of the contents is substantially inconsistent with the predetermined state.

Figure 4:
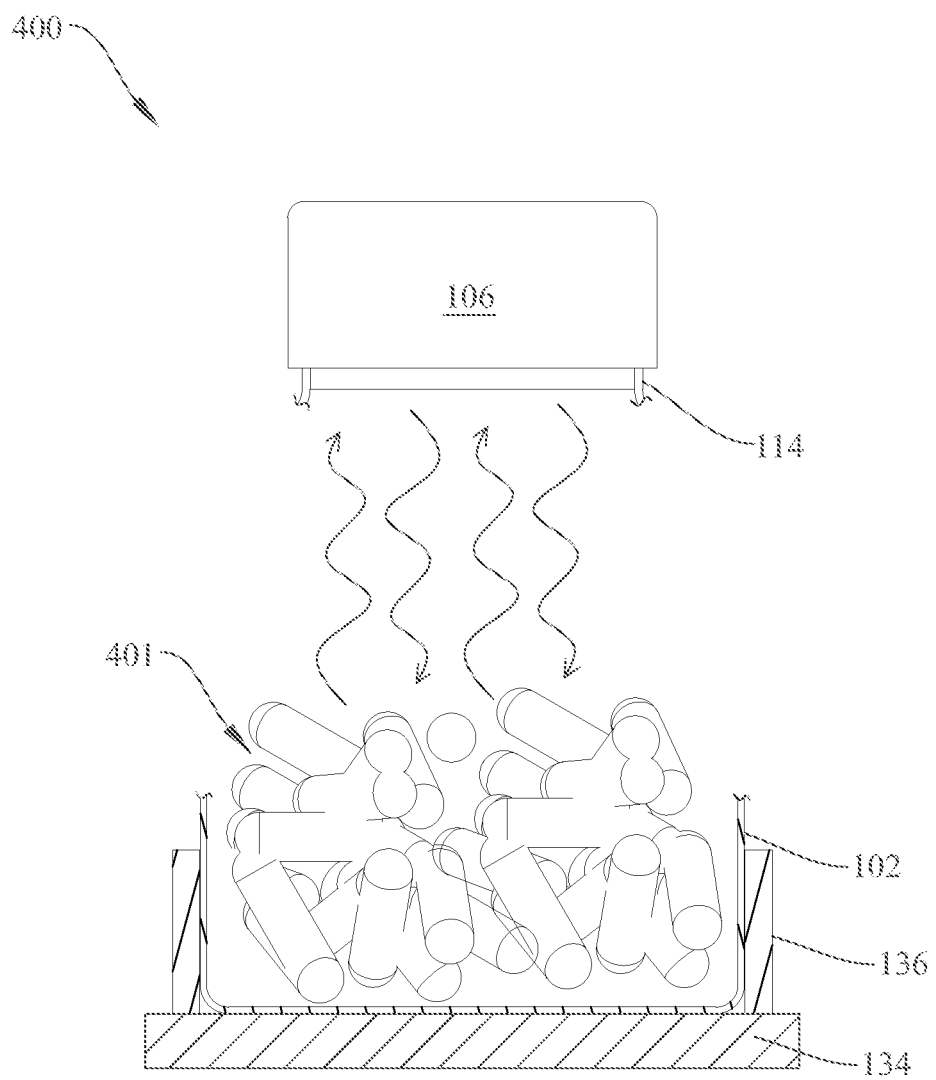
FIG. 4 is a schematic, simplified, partial cross-sectional view of a solid contents verification system according to one embodiment.

FIG. 4 shows a schematic representation of the solid contents verification system system 100 that includes cutaway and cross section representations. The container 102 is positioned and held by the container chamber 132 of the base 134 of the container-carrying unit 110. The contents sensor 114 emit measurement signals, e.g., sound, electromagnetic signals or both, which are shown as the downwardly extending arrows in FIG. 4. In this example, the emitted signals are directed essentially vertically into the open top of the container. The emitted signals enter the open top of the container 102 and impinge the contents 401, here shown as pills, capsules, or tablets. However, other dry goods may be the contents in the container 102. The top surface of the contents 401 is not a smooth or regular surface. Accordingly, the return signal to reflected signal (the up arrows in FIG. 4) can take different times to return to contents sensor 114. Moreover, the irregular surface of the contents 401 will cause some of the return signals to travel at an angle on the return and increase the return time. Some return signals may miss the contents sensor 114 completely. Other signals may bounce off (e.g., impinge) the walls of the container or off other contents before returning to the contents sensor 114, if at all. Each of these impingements can change the characteristics of the return signal. The measurement signal can also have part of its energy absorbed by the contents. The measurement signal can also be spectrum shifted or have its pulse width or frequency altered by the contents. The processor or circuitry in the solid contents verification system 100 can account for the differences in the return signal to the contents sensor 114 in view of the emitted signal from the contents sensor 114.

In some embodiments, the contents sensor 114 transmits a voltage feedback signal to the control unit 202. Voltage values for various types of contents at various fill levels (e.g. empty and full) in the containers 102 are stored at the information module 210. After obtaining identification of the container 102 via the second image sensor 122, the information from the identification, such as container size and number of contents, is used to find the expected voltage value, stored at the information module 210, corresponding with the desired state of the contents in the container 102. The comparator module 208 gives either a pass or fail signal after comparing the voltage reading to the stored voltage value. Thus, feedback is given on the state of the contents and the control unit 202 instructs the conveyor unit 108 according to the feedback. In the event of a fail signal, the container 102 is flagged or marked and the conveyor unit 108 may route the container 102 to a pharmacist for inspection.

In some embodiments, the system includes a contents sensor unit, a contents-carrying unit, a control unit and a conveyor unit. The contents sensor unit includes a contents sensor configured to send and receive sonic pulses to determine a state of contents in a container. The contents sensor unit is configured to send a signal communicating a state of the contents in a container. The container-carrying unit is configured to hold a container in substantial alignment with the contents sensors to expose the contents to the sonic pulses. The control unit is operatively connected to the contents sensor unit. The control unit is configured to receive the signal communicating the state of the contents and to compare the state of the contents with a desired state of the contents. The conveyor unit is operatively connected to the container-carrying unit. The conveyor unit is configured to move the container-carrying unit and stop the container-carrying unit at a verification point, which is proximal the contents sensors, to substantially align with the contents sensors.

In some embodiments, the method includes aligning an opening of a container with a content sensor at a verification point; directing sonic pulses at the opening of the container; receiving reflected sonic pulses by the content sensor; determining a state of the contents in the container from the reflected sonic pulses; comparing the state of the contents with a desired state of the contents to assess at least one characteristic of the contents; and routing the container based on the at least one characteristic of the contents.

GENERAL INTERPRETATION OF TERMS

In understanding the scope of embodiments of the present invention, the term "comprising" and its derivatives, as used herein, are intended to be open ended terms that specify the presence of the stated features, elements, components, groups, and/or steps, but do not exclude the presence of other unstated features, elements, components, groups, and/or steps. The foregoing also applies to words having similar meanings such as the terms, "including", "having" and their derivatives. Also, the terms "part," "component," "portion," "member" or "module" when used in the singular can have the dual meaning of a single part or a plurality of parts. As used herein to describe embodiments of the present invention, the following directional terms "forward, rearward, above, downward, vertical, horizontal, below and transverse" as well as any other similar directional terms refer to those directions of the system 100 and method 300 in a normal operating position. As used herein, "a" or "an" may reflect a single part or multiple parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies. Other ranges of deviation may be within the scope of the embodiments of the present invention. The term "based on" or using, as used herein, reflects an open-ended term that can reflect others elements beyond those explicitly recited.

While only selected embodiments have been chosen to illustrate embodiments of the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A system comprising:
   at least one contents sensor configured to:
      send and receive sonic pulses or electro-magnetic signals to determine a state of contents in a container, and
      send a signal representing the state of the contents in the container, the contents being a plurality of solids that form an irregular top surface in the container; and
   a verification processor configured to:
      receive the signal representing the state of the contents,
      compare the state of the contents with an expected state of the contents,
      record a verification of the container in response to the state of the contents being consistent with the expected state of the contents, and
      flag the container in response to the state of the contents being not consistent with the expected state of the contents.

2. The system of claim 1, further comprising a conveyor configured to:
   move the container to be close to or away from the at least one contents sensor for sending or receiving the sonic pulses or electro-magnetic signals; or
   stop the movement of the container at a verification point.

3. The system of claim 1, wherein the at least one contents sensor includes a sound pulse device configured to send and receive the sonic pulses.

4. The system of claim 3, wherein the sound pulse device includes an ultrasonic sensor.

5. The system of claim 3, wherein the sound pulse device includes separate transducers configured to send and receive the sonic pulses separately.

6. The system of claim 3, wherein the sound pulse device includes a transceiver configured to both send and receive the sonic pulses.

7. The system of claim 6, wherein the transceiver is configured to translate the received sonic pulses into an electrical signal.

8. The system of claim 7, wherein the transceiver includes a circuitry to determine a distance to:
   a reflective upper surface of the contents in the container when the container is not empty; or
   a bottom of the container when the container is empty.

9. The system of claim 8, wherein the distance is analyzed to determine the state of the contents.

10. The system of claim 1, wherein the at least one contents sensor includes at least one photo diode or at least one CMOs detector configured to send and receive the electro-magnetic signals.

11. The system of claim 1, wherein the state of contents includes at least one or more of the following:
   a fill level of an upper surface of the contents of the container;
   a quantity of the contents of the container;
   a presence or no presence of the contents of the container;
   a shape of the contents;
   a color of the contents; and
   a type of the contents.

12. The system of claim 11, wherein:
the contents are multiple small, pellet-like, pharmaceutical solid materials,
the at least one contents sensor further includes a first image sensor configured and arranged to acquire a first image of the contents in the container, and
the verification processor is configured to analyze the first image to determine the shape, the color, or the shape and the color of the contents in the container and comparing the shape, the color, or the shape and the color respectively with the expected state.

13. The system of claim 12, wherein:
the at least one contents sensor further includes a second image sensor configured and arranged to acquire a second image of a label on an exterior surface of the container, and
the verification processor is configured to analyze the second image to determine characteristics of the contents to access the expected state based on container-specific information on the label.

14. The system of claim 13, wherein the container-specific information includes at least one or more of the following:
a container size;
a type of the contents;
a name of the contents; and
an expected quantity of the contents for the container.

15. The system of claim 1, wherein:
the signal is a voltage value,
the expected state is represented by an expected voltage value according to container-specific information, and
the voltage value is compared with the expected voltage value to determine the state of the contents.

16. A method comprising:
directing a plurality of sonic pulses or electro-magnetic signals toward an opening of a container;
detecting a plurality of reflected sonic pulses or reflected electro-magnetic signals reflected from an irregular top surface formed by a plurality of solids contained in the container or a bottom of the container when the container is empty;
determining a state of the plurality of solids based on the plurality of reflected sonic pulses or reflected electro-magnetic signals;
comparing the state with an expected state of the plurality solids to obtain a comparison result;
recording a verification of the container in response to the comparison result indicating that the state is consistent with the expected state; and
flagging the container in response to the comparison result indicating that the state is not consistent with the expected state.

17. The method of claim 16, further comprising:
routing the container for inspection when the container is flagged.

18. The method of claim 16, wherein the plurality of solids is a plurality of small, pellet-like, pharmaceutical solid materials, the method further comprising:
acquiring a first image of the plurality of solids contained in the container;
analyzing the first image to determine a shape or a color of the plurality of solids; and
comparing the determined shape or the determined color with an expected shape or color representing the expected state.

19. The method of claim 18, further comprising:
acquiring a second image of a label on an exterior surface of the container; and
analyzing the second image to determine characteristics of the plurality of solids to access the expected state based on container-specific information on the label.

20. The method of claim 19, wherein the container-specific information includes at least one or more of the following:
a container size;
a type of the contents;
a name of the contents; and
an expected quantity of the contents for the container.

21. The method of claim 16, wherein the plurality of reflected sonic pulses includes at least one ultrasonic pulse.

22. The method of claim 16, wherein the plurality of electro-magnetic signals includes a microwave signal pulse, a pulsed radar signal, or a combination thereof.

* * * * *